United States Patent
Fraser et al.

(10) Patent No.: US 10,448,924 B2
(45) Date of Patent: Oct. 22, 2019

(54) ULTRASONIC ACOUSTIC RADIATION FORCE EXCITATION FOR ULTRASONIC MATERIAL PROPERTY MEASUREMENT AND IMAGING

(75) Inventors: John Douglas Fraser, Woodinville, WA (US); Roy Peterson, Seattle, WA (US); Jean-Luc Robert, White Plains, NY (US); Vijay Shamdasani, Seattle, WA (US); Hua Xie, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 383 days.

(21) Appl. No.: 13/992,281

(22) PCT Filed: Dec. 2, 2011

(86) PCT No.: PCT/IB2011/055437
§ 371 (c)(1),
(2), (4) Date: Sep. 19, 2013

(87) PCT Pub. No.: WO2012/080895
PCT Pub. Date: Jun. 21, 2012

(65) Prior Publication Data
US 2014/0005548 A1  Jan. 2, 2014

Related U.S. Application Data

(60) Provisional application No. 61/422,468, filed on Dec. 13, 2010.

(51) Int. Cl.
*A61B 8/00* (2006.01)
*A61B 8/08* (2006.01)
*G01S 7/52* (2006.01)

(52) U.S. Cl.
CPC .......... *A61B 8/4483* (2013.01); *A61B 8/4488* (2013.01); *A61B 8/461* (2013.01);
(Continued)

(58) Field of Classification Search
None
See application file for complete search history.

(56) References Cited

U.S. PATENT DOCUMENTS

| 5,810,731 A | 9/1998 | Sarvazyan et al. |
| 7,374,538 B2 * | 5/2008 | Nightingale et al. ......... 600/443 |

(Continued)

FOREIGN PATENT DOCUMENTS

WO  2009140607 A1  11/2009

OTHER PUBLICATIONS

Fronheiser, Matthew P., et al. "4K-2 3D Acoustic Radiation Force Impulse (ARFI) Imaging using a 2D Matrix Array: Feasibility Study." Ultrasonics Symposium, 2006. IEEE. IEEE, 2006.*

(Continued)

*Primary Examiner* — Carolyn A Pehlke
(74) *Attorney, Agent, or Firm* — Sherry Austin

(57) ABSTRACT

An ultrasonic diagnostic imaging system for shear wave measurement transmits push pulses in the form of a sheet of energy. The sheet of energy produces a shear wavefront which is a plane wave, which does not suffer from the 1/R radial dissipation of push pulse force as does a conventional push pulse generated along a single push pulse vector. The sheet of energy can be planar, curved, or in some other two or three dimensional shape. A curved sheet of energy can produce a shear wave source which focuses into a thin line, which increases the resolution and sensitivity of the measuring techniques used to detect the shear wave effect.

14 Claims, 6 Drawing Sheets

(52) U.S. Cl.
CPC ............ *A61B 8/485* (2013.01); *A61B 8/5276* (2013.01); *G01S 7/5202* (2013.01); *G01S 7/52042* (2013.01); *G01S 7/52046* (2013.01); *A61B 8/0825* (2013.01)

(56) References Cited

U.S. PATENT DOCUMENTS

| | | | |
|---|---|---|---|
| 7,713,203 B2* | 5/2010 | Lacoste et al. | 600/439 |
| 2003/0158483 A1 | 8/2003 | Jackson et al. | |
| 2008/0249408 A1 | 10/2008 | Palmeri et al. | |
| 2008/0276709 A1* | 11/2008 | Bercoff et al. | 73/606 |
| 2009/0124901 A1* | 5/2009 | Fink et al. | 600/437 |
| 2010/0069751 A1 | 3/2010 | Hazard et al. | |
| 2010/0191113 A1 | 7/2010 | Hazard et al. | |
| 2010/0286520 A1 | 11/2010 | Hazard et al. | |
| 2011/0028838 A1* | 2/2011 | Pernot | A61B 5/0048 600/437 |
| 2011/0066030 A1* | 3/2011 | Yao | A61B 5/0048 600/438 |
| 2012/0134233 A1* | 5/2012 | Lin et al. | 367/7 |

OTHER PUBLICATIONS

Bercoff, Jérémy, Mickaël Tanter, and Mathias Fink. "Supersonic shear imaging: a new technique for soft tissue elasticity mapping." Ultrasonics, Ferroelectrics, and Frequency Control, IEEE Transactions on 51.4 (2004): 396-409.*

Peter R. Hoskins, Kevin Martin, Abigail Thrush, "Diagnostic Ultrasound: Physics and Equipment", Cambridge University Press, Jun. 17, 2010.*

Fink, Mathias, and Mickael Tanter. "Multiwave imaging and super resolution." Physics Today 63.2 (2010): 28-33.*

Fenster, Aaron, and Donal B. Downey. "3-D ultrasound imaging: A review." IEEE Engineering in Medicine and Biology magazine 15.6 (1996): 41-51.*

Fahey et al: "Acoustic Radiation Force Impulse Imaging of the Abdomen: Demonstration of Feasibility and Utility"; Ultrasound in Medicine and Biology, vol. 31, No. 9, Sep. 2005, pp. 1185-1198.

Tanter et al: "Quantitative Assessment of Breast Lesion Viscoelasticity: Initial Clinical Results Using Supersonic Shear Imaging"; Ultrasound in Medicine and Biology, vol. 34, No. 9, Sep. 2008, pp. 1373-1386.

Sarvazyan et al: "Shear Wave Elasticity Imaging: A New Ultrasonic Technology of Medical Diagnostics"; Ultrasound in Medicine and Biology, vol. 24, No. 9, pp. 1419-1435, 1998.

Fatemi et al: "Ultrasound-Stimulated Vibro-Acoustic Spectrography"; Science 280, vol. 82, 1998, pp. 82-85.

Palmeri et al: "Quantifying Hepatic Shear Modulus In Vivo Using Acoustic Radiation Force"; Ultrasound in Medicine and Biology, Apr. 2008, Issue 34 (4): pp. 546-558.

Urban et al: "Error in Estimates of Tissue Material Properties From Shear Wave Dispersion Ultrasound Vibrometry:" IEEE Transactions in Ultrason Ferroelectric Freq Control, Apr. 2009, 56(4): pp. 748-758.

Nightingale et al: "On the Feasibility of Remote Palpation Using Acoustic Radiation Force"; 2001 Acoustical Society of America, vol. 110, No. 1, pp. 625-634.

Bouchard et al: "Image Quality, Tissue Heating, and Frame Rate Trade-Offs in Acoustic Radiation Force Impulse Imaging"; IEEE Transactions on Ultrasonics, Ferroelectrics, and Frequency Control, vol. 56, No. 1, Jan. 2009, pp. 63-76.

\* cited by examiner

ULTRASONIC ACOUSTIC RADIATION FORCE EXCITATION FOR ULTRASONIC MATERIAL PROPERTY MEASUREMENT AND IMAGING

This invention relates to medical diagnostic ultrasound systems and, in particular, to ultrasound systems which perform measurements of tissue stiffness or elasticity using shear waves.

Various means of remotely interrogating tissue mechanical properties for diagnostic purposes have been developed that exploit the radiation force of an ultrasonic beam to apply force remotely to a region of tissue within the body of the patient (acoustic radiation force; also referred to as "push" pulses). Acoustic radiation force can be applied in such a way that elastic properties may be measured, either locally at the point of deformation by tracking the deformation directly through the use of further ultrasonic imaging to follow the pattern of deformation quasi-statically and visually discern regions of varying stiffness. See, for example, Nightingale, K. R. et al, "On the feasibility of remote palpation using acoustic radiation force", *J. Acoust. Soc. Am.*, vol. 110 no. 1 (2001), pp. 625-34; and M. L Palmieri et al. The deformation caused by the acoustic radiation force can also be used as a source of shear waves propagating laterally away from the deformed region, which may then be imaged to interrogate adjacent regions for their material properties through time-domain shear wave velocity imaging. See, in this regard, Sarvazyan, A. et al., "Shear wave elasticity imaging: A new ultrasonic technology of medical diagnostics", *Ultrasound Med. Biol.* 24, pp 1419-1435 (1998) and "Quantifying Hepatic Shear Modulus In Vivo Using Acoustic Radiation Force", *Ultrasound in Med. Biol.*, vol. 34, 2008. This technique can also be used to assess frequency-domain shear wave modulus and viscosity. See Fatemi, M. et al., "Ultrasound-stimulated vibro-acoustic spectrography", *Science* 280, pp 82-85 (1998). These techniques use a one dimensional array transducer to generate the shear waves and are thus hampered by limited effective depth of penetration by a combination of weak coupling and safety limits imposed on the maximum power of the excitation beams, combined with unfavorable diffraction effects that limit the penetration depth for effective measurement. See Bouchard, R. et al., "Image Quality, Tissue Heating, and Frame Rate Trade-offs in Acoustic Radiation Force Impulse Imaging", *IEEE Trans. UFFC* 56, pp 63-76 (2009).

Additionally, the existing techniques, due to the limited extent of the push pulse excitation and the two dimensional imaging methodology, are incapable of discriminating between regions of property variations within the plane of imaging and those which may lie near but out of the plane. The mixing of these out-of-plane property values with in-plane values during the imaging process may lead to unnecessary reduction of accuracy and diagnostic value in the output of these techniques.

In conventional acoustic radiation force imaging and point quantification as presently practiced, the push is generated by a 1-D array that produces a beam which may be well controlled in the single imaging plane, but is restricted to a single, moderately tight focus in the cross, or elevation plane, by a fixed focus mechanical lens. This leads to a mechanical push force which creates a response laterally in all directions, in and out of the plane of the array. The tissue motion elicited by this push propagates generally radially in all lateral directions, and suffers a fall off as a factor of 1/R in the radial directions (in the instance of a line source in the push pulse direction) in addition to normal attenuation caused by tissue viscosity. In the case of acoustic radiation force qualitative and quantitative imaging, this is deleterious because out-of-plane regions of stiffness variation will contribute to the axial displacement in the image plane, confounding the accuracy of the stiffness measurement in the image plane. In the case of point quantification, the radial propagation disburses useful shear wave energy away from the imaging plane, reducing the signal amplitude needed for accurate property estimation.

The motion produced by acoustic radiation force transmission within diagnostic emission limits is very small, on the order of 0.1 to 15 micrometers in amplitude. The measurement of such tiny motions is accomplished by tracking the reflections from local inhomogeneities in the tissue being studied, which means that the received signal effects of a shear wave can be difficult to discriminate. In addition, shear wave motion is heavily damped in tissue, which is viscoelastic in character. Thus, an adequate signal-to-noise ratio is difficult to obtain, and penetration range is very limited. Any interfering signals will adversely affect the results. A significant source of interference is relative motion of the transducer being used for the study and the region of tissue being studied. This can be caused by external sources such as unsteadiness of the operator's hand, or internal sources such as breathing, heartbeats, or other voluntary or involuntary movement of the subject. Prior art attempts at signal-to-noise improvement for acoustic radiation force techniques would bandpass filter the signals to eliminate the lower frequencies from the data. Most of the motion artifacts are below 50 Hz, so some improvement can be made. See, for example, Urban et al, "Error in Estimates of Tissue Material Properties from Shear Wave Dispersion Ultrasound Vibrometry," *IEEE Trans. UFFC*, vol. 56, No. 4, (April 2009). However, some of this interference is quite large in amplitude, and bandpass filtering is not always sufficient to eliminate the adverse effects. Artifacts in the form of mis-estimated displacements and hence miscalculated shear wave velocities and moduli are common.

Accordingly, it is an object of the present invention to improve the effective depth of penetration of acoustic radiation force effects such as shear waves. It is a further object of the present invention to reduce out-of-plane effects during material assessment. It is a further object of the present invention to reduce measurement errors due to the relative motion of the transducer in acoustic radiation force-based studies.

In accordance with the principles of the present invention, a diagnostic ultrasonic imaging system and method are described which enables a user to acquire highly resolved image data sufficient to measure tissue motion or the characteristics of a shear wave propagating through tissue. An ultrasound probe with a two dimensional array of transducer elements transmits a push pulse in the form of a sheet of energy into tissue. The sheet of energy can be planar or non-planar, and can be produced by a sequence of individually transmitted ultrasound pulses or by transmission of a plane wavefront. Unlike the single vector push pulses of the prior art, the two dimensional push pulse of the sheet of energy produces a planar or semi-planar shear wavefront which does not suffer from the 1/R falloff of energy spread of the prior art techniques. In accordance with a further aspect of the present invention, a plurality of background tracking pulses are transmitted about the location of a push pulse and the field of interest in which a shear wave is to be detected. Echo signals received from the background tracking pulses are correlated over time to estimate background motion in the field of interest during propagation of the shear wave, which is used to adjust the measured displacement caused by passage of the shear wave.

Figure 3:
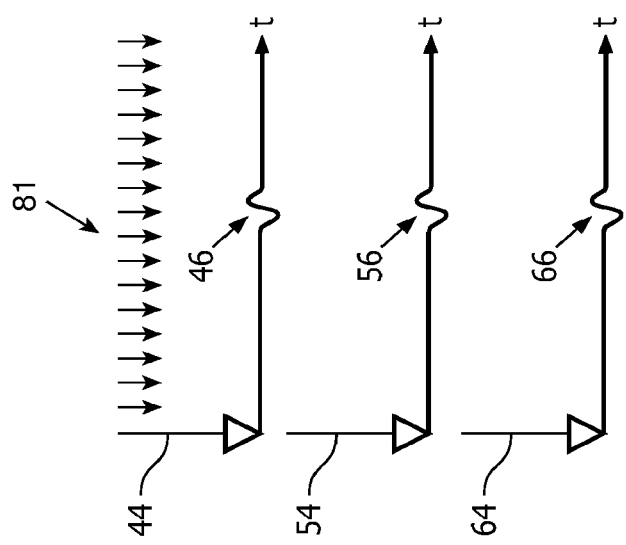

FIG. 3 spatially illustrates a sequence of pulse pulses along a push pulse vector, the resultant shear wavefront, and a series of tracking pulse vectors.

Figure 4:
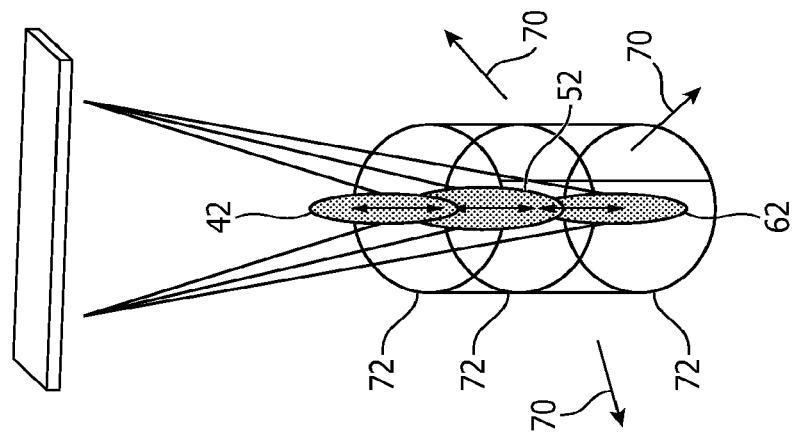

FIG. 4 illustrates the radial spread of a shear wavefront emanating from a push pulse vector.

Figure 5:
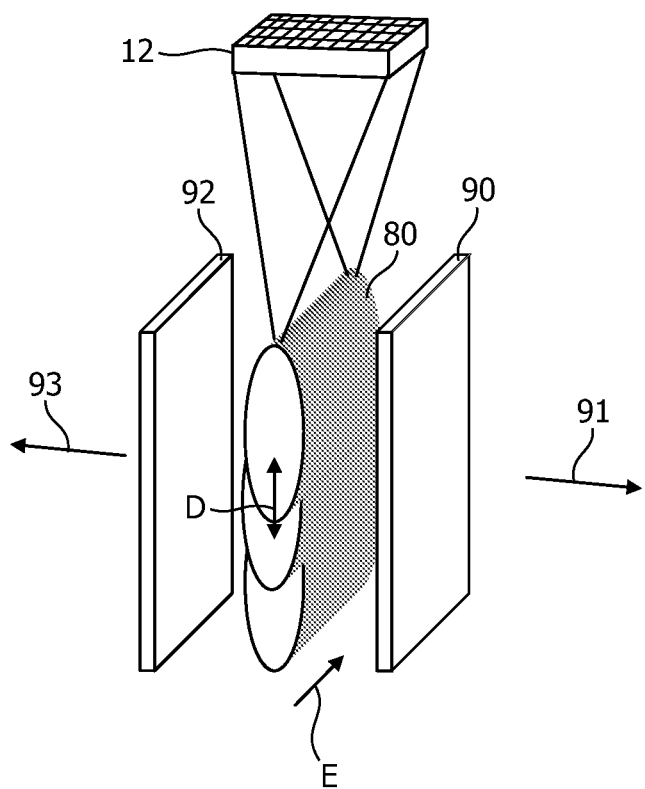

FIG. 5 illustrates a two dimensional push pulse produced in accordance with the principles of the present invention.

Figure 6:
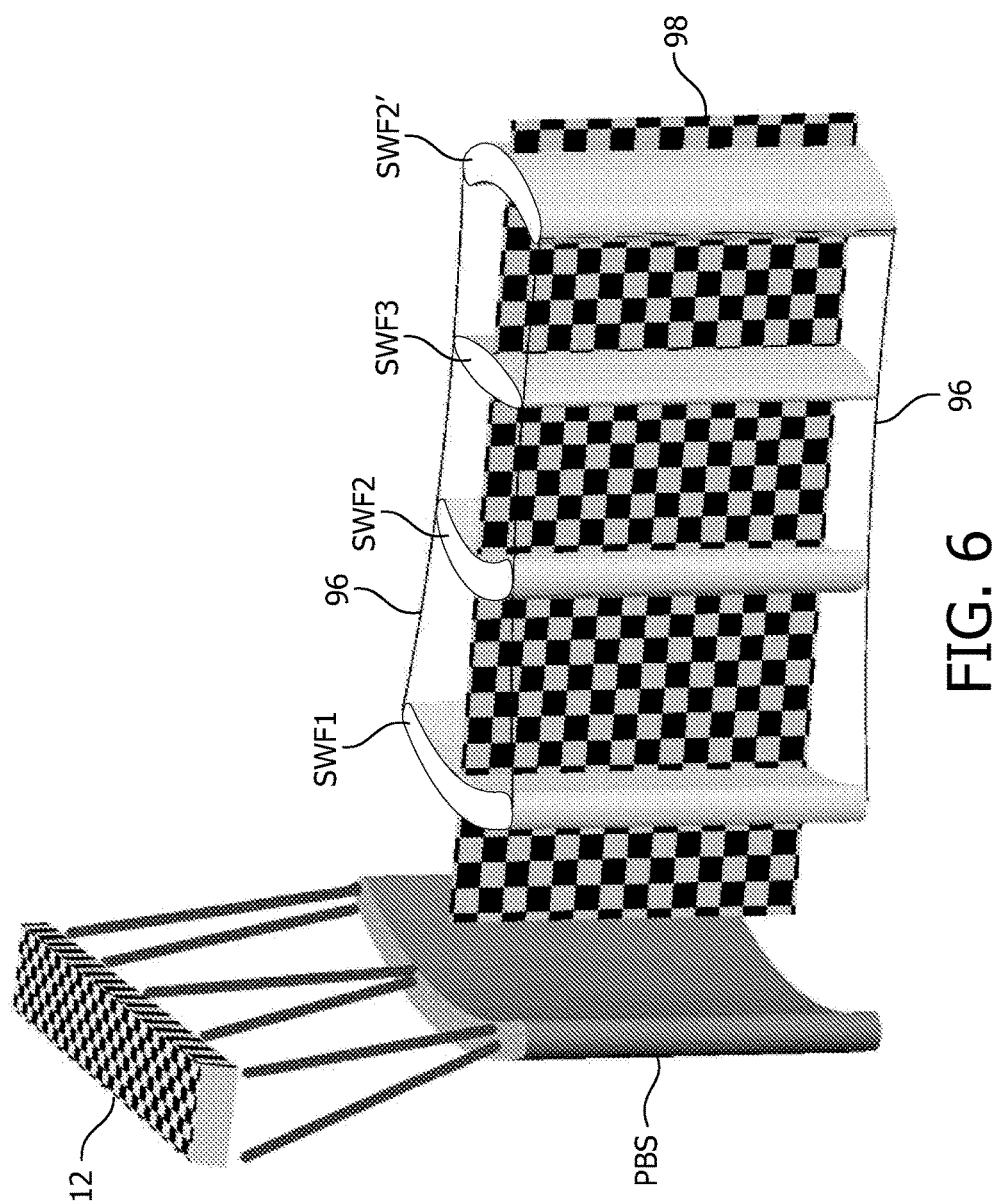

FIG. 6 illustrates a curved two dimensional push pulse produced in accordance with the principles of the present invention.

Figure 7:
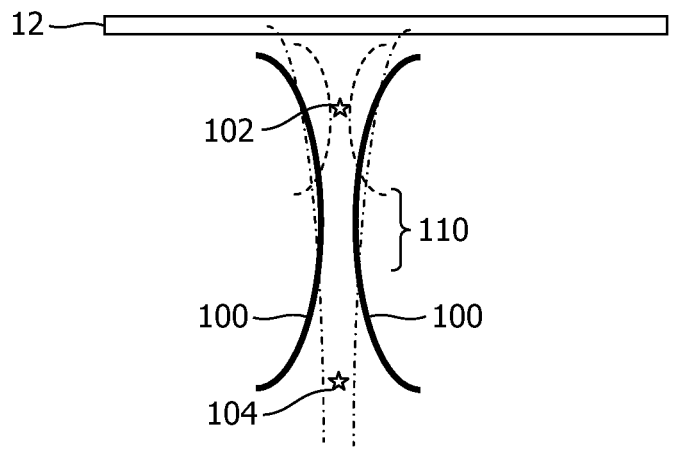
Figure 8:
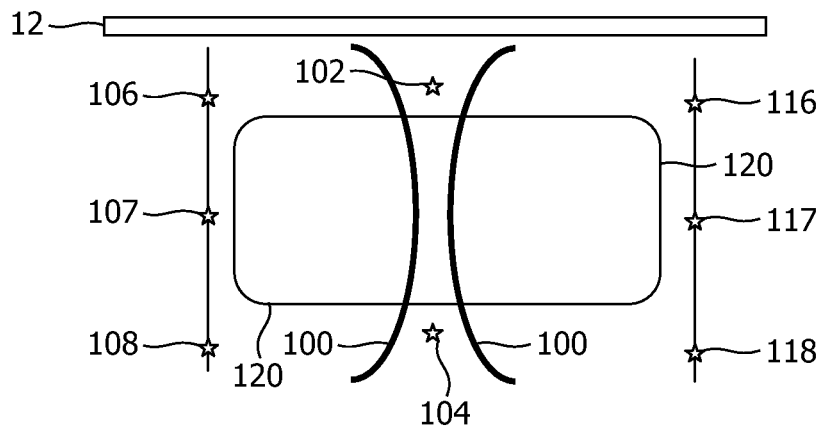
Figure 9:
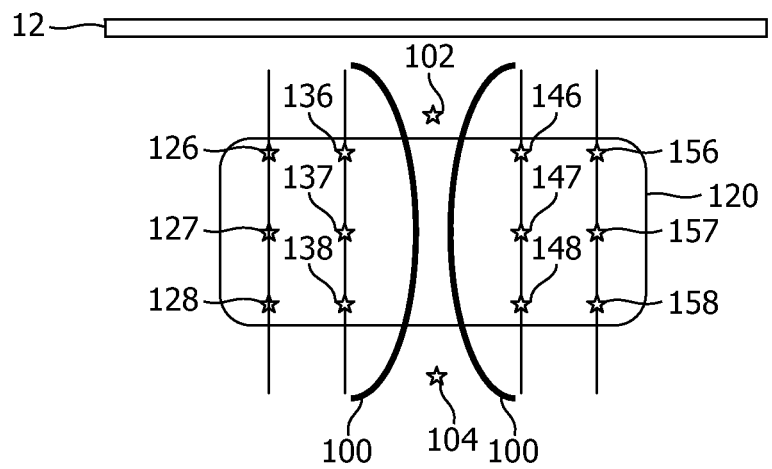

FIGS. 7-9 illustrate the use of background tracking pulses to estimate background tissue motion in the region of a shear wave in accordance with the principles of the present invention.

Figure 1:
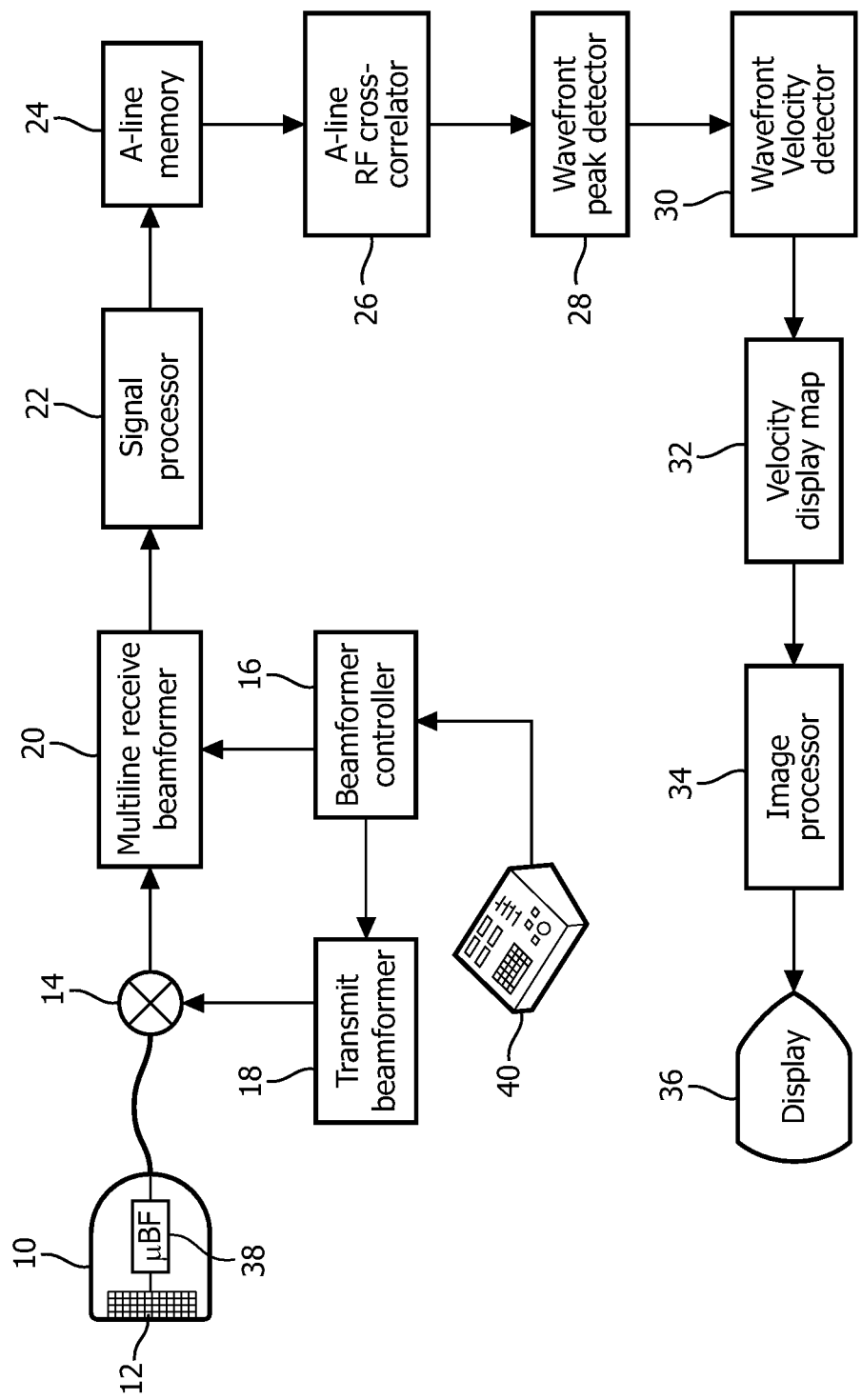
FIG. 1 illustrates in block diagram form an ultrasonic diagnostic imaging system constructed in accordance with the principles of the present invention.

Referring first to FIG. 1, an ultrasound system constructed in accordance with the principles of the present invention for the measurement of shear waves is shown in block diagram form. An ultrasound probe 10 has a two dimensional array 12 of transducer elements for transmitting and receiving ultrasound signals. A two dimensional array transducer can scan a two dimensional (2D) plane by transmitting beams and receiving returning echo signals over a single plane in the body and can also be used to scan a volumetric region by transmitting beams in different directions and/or planes of a volumetric (3D) region of the body. The array elements are coupled to a micro-beamformer 38 located in the probe which controls transmission by the elements and processes the echo signals received from groups or sub-arrays of elements into partially beamformed signals. The partially beamformed signals are coupled from the probe to a multiline receive beamformer 20 in the ultrasound system by a transmit/receive (T/R) switch 14. Coordination of transmission and reception by the beamformers is controlled by a beamformer controller 16 coupled to the multiline receive beamformer and to a transmit controller 18, which provides control signals to the micro-beamformer. The beamformer controller is responsive to signals produced in response to user manipulation of a user control panel 40 to control the operation of the ultrasound system and its probe.

The multiline receive beamformer 20 produces multiple, spatially distinct receive lines (A-lines) of echo signals during a single transmit-receive interval. The echo signals are processed by filtering, noise reduction, and the like by a signal processor 22, then stored in an A-line memory 24. Temporally distinct A-line samples relating to the same spatial vector location are associated with each other in an ensemble of echoes relating to a common point in the image field. The r.f. echo signals of successive A-line sampling of the same spatial vector are cross-correlated by an A-line r.f. cross-correlator 26 to produce a sequence of samples of tissue displacement for each sampling point on the vector. Alternatively, the A-lines of a spatial vector can be Doppler processed to detect shear wave motion along the vector, or other phase-sensitive techniques such as speckle tracking in the time domain can be employed. A wavefront peak detector 28 is responsive to detection of the shear wave displacement along the A-line vector to detect the peak of the shear wave displacement at each sampling point on the A-line. In a preferred embodiment this is done by curve-fitting, although cross-correlation and other interpolative techniques can also be employed if desired. The time at which the peak of the shear wave displacement occurs is noted in relation to the times of the same event at other A-line locations, all to a common time reference, and this information is coupled to a wavefront velocity detector 30 which differentially calculates the shear wave velocity from the peak displacement times on adjacent A-lines. This velocity information is coupled into a velocity display map 32 which indicates the velocity of the shear wave at spatially different points in a 2D or 3D image field. The velocity display map is coupled to an image processor 34 which processes the velocity map, preferably overlaying the anatomical ultrasound image of the tissue, for display on an image display 36.

Figures 2A, 2B, 2C:
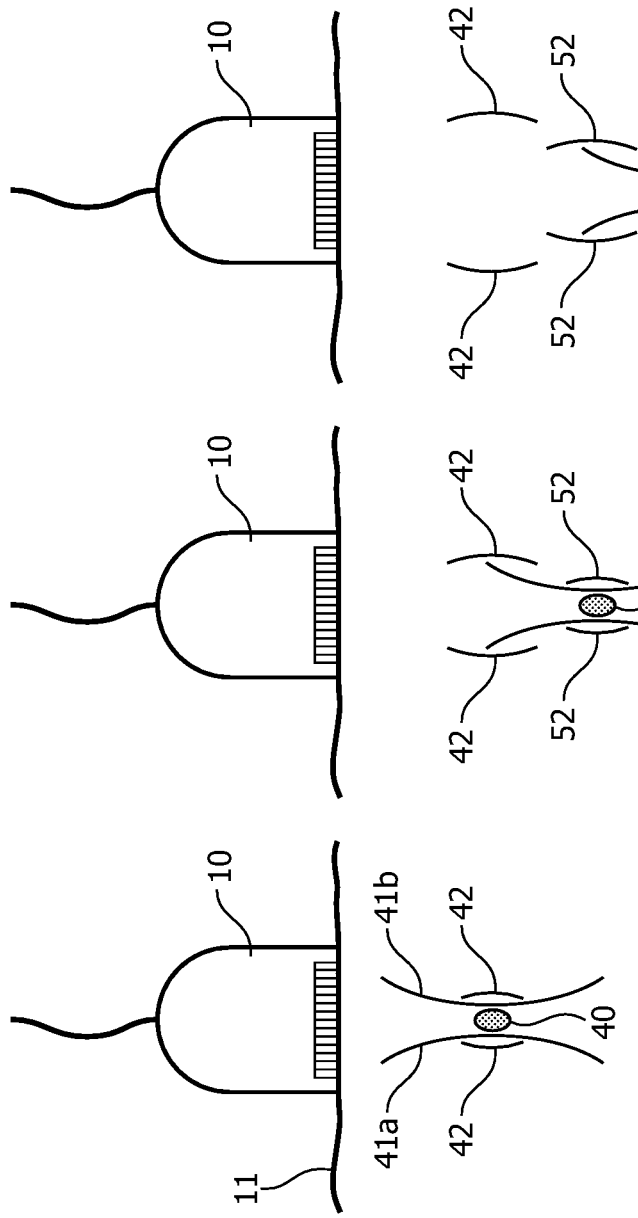
FIGS. 2a-2c illustrate the transmission of a sequence of push pulses to different depths to produce a shear wavefront.

FIGS. 2a-2c illustrate the transmission of a sequence of focused high MI (Mechanical Index) push pulses (e.g., MI of 1.9 or less so as to be within FDA diagnostic limits) along a single vector direction to produce a shear wavefront. Pulses of high MI and long durations are used so that sufficient energy is transmitted to displace the tissue downward along the transmit vector and cause the development of a shear wave. In FIG. 2a the probe 10 at the skin surface 11 transmits a first push pulse 40 into the tissue with a beam profile 41a, 41b to a given focal depth indicated by the shaded area 40. This push pulse will displace the tissue at the focus downward, resulting in a shear wavefront 42 emanating outward from the displaced tissue.

FIG. 2b illustrates a second push pulse 50 transmitted by the probe 10 along the same vector and focused at the deeper depth of the shaded area 50. This second push pulse 50 displaces the tissue at the focal depth, causing a shear wavefront 52 to emanate outward from the displaced tissue. Thus, shear wavefronts 42 and 52 are both propagating laterally through the tissue, with the initial wavefront 42 preceding the second as a function of the time interval between the transmission of the two push pulses and the propagation delay difference due to the change in propagation distance to the focus.

FIG. 2c illustrates the transmission by probe 10 of a third push pulse 60 at a greater depth which produces an outward emanating shear wavefront 62. It is seen in FIG. 2c that the composite wavefront of the three push pulses, indicated by the composite wavefront profile of 42, 52, and 62, extends for an appreciable depth in the tissue, from the shallow depth of the first push pulse 40 to the deepest depth of the third push pulse 60. This enables shear wave measurement over an appreciable depth of tissue. In an implementation of the system of FIG. 1, a push pulse sequence such as this can be used to detect shear wave propagation over a depth of 6 cm., a suitable depth for breast mass imaging and diagnosis.

It will be appreciated that a greater or lesser number of push pulses can be transmitted along the push pulse vector, including a single push pulse. Multiple push pulses can be transmitted in any order, with the order determining the shape and direction of the composite shear wavefront. For example, if the push pulses of FIGS. 2a-2c were transmitted in sequence from the deepest (60) to the shallowest (40) with appropriate delays between transmits, the composite shear wavefront of FIG. 2c would have the inverse tilt to that shown in FIG. 2c. Typically, each push pulse is a long pulse of 50 to 200 microseconds in duration. A typical duration is 100 microseconds, for instance. The ultrasound produced during the 100 microsecond pulse duration are compressional wave pulses and can have a frequency of 7 or 8 MHz, for example. The push pulses are well focused, preferably at an f number of 1 to 2. In one typical implementation, a push pulse is transmitted every 2.5 milliseconds (as long as the shear source moving speed from (40) to (50) and (50) to (60) is greater than the shear wave propagation speed), giving the push pulses a 400 Hz transmission frequency. In another implementation, all three push pulses are transmitted in one sequence to launch the full shear wavefront before the tracking A-lines begin.

FIG. 3 is another illustration of the use of three push pulses to create a composite shear wavefront. The three push pulses are transmitted along vectors 44, 54, and 64 which are seen to be aligned along a single vectorial direction in FIG. 3. When the deepest push pulse of vector 64 is transmitted first followed by push pulses focused at successively shallower depths, the shear wavefronts of the respective push pulses will have propagated as indicated by waves 46, 56, and 66 by a time shortly after the last push pulse (vector 64) has been transmitted. The time intervals between the transmit times of the push pulses is determined by the shear and longitudinal velocities, because the propagation time to the focus needs to be taken into account. As the shear waves 46, 56, and 66 travel outward from the push pulse vector, they are interrogated by tracking pulses 81 shown in spatial progression along the top of the drawing. Tracking pulses can occur between as well as after push pulses. Unlike the depiction of FIG. 2c, the illustration of the shear waves 46, 56, and 56 of the composite wavefront of FIG. 3 shows the propagated shear waves to be substantially aligned in time and horizontal propagation distance. From the perspective of the dramatic difference in propagation speed between the longitudinal push pulses and shear waves in tissue, on the order of 100 to 1, this is a representative depiction when the individual push pulses are transmitted in rapid succession. Since the sole function of the push pulses is to effect a force on tissue and no following time period is needed for echo reception as is the case with pulse-echo ultrasound imaging, substantially no dead time is required following each pulse and the push pulses can be transmitted in very rapid succession. The transit time of a push pulse in tissue is on the order of 100 microseconds (ultrasound travels at a speed of about 1560 meters/sec in tissue), whereas a shear wave period in tissue is on the order of 2 to 10 milliseconds (shear waves travel at a speed of about 1-5 meters/sec in tissue). Thus, from the perspective of the periodicity and speed of a shear wave, a rapid succession of push pulses is near instantaneous, producing a single wavefront.

In conventional acoustic radiation force imaging and point quantification, the push pulse(s) are transmitted along a single vector direction. When the push is generated by a 1-D array, a transducer having a single line of transducer elements, the array produces a beam which may be well controlled in the single imaging plane of the array, but is restricted to a single, moderately tight focus in the cross, or elevation plane by the fixed focus mechanical lens of the probe. This leads to a mechanical push which creates a response which radiates laterally in all directions, in and out of the single imaging plane of the array. The tissue motion elicited by this push energy propagates roughly radially in all lateral directions as illustrated by the circular wavefronts 72 surrounding the push pulse vector and the outward-radiating arrows 70 in FIG. 4, and suffers a fall-off in energy as a function of 1/R in the radial directions in addition to normal tissue attenuation. In the case of acoustic radiation force qualitative and quantitative imaging, this is deleterious because out-of plane regions of stiffness variation will contribute to the tissue axial displacement in the image plane, confounding the accuracy of the stiffness measurement in the image plane. In the case of acoustic radiation force point quantification, the radial propagation removes useful shear wave energy from the imaging plane, reducing the signal amplitude needed for property estimation.

In accordance with the principles of the present invention, the push pulse is formed as a two dimensional sheet of energy rather than a single one dimensional vector. Such two dimensional push beam sheets extend in the depth dimension D and also in the elevation or azimuth dimension E as illustrated by push beam sheet 80 in FIG. 5. The push beam sheet 80 results in the generation of shear waves with planar wavefronts as indicated by plane wavefronts 90, 92 in FIG. 5, which travel laterally from the force field of the push beam sheet 80 as indicated by arrows 91, 93. This shear wave excitation is like a plane wave source rather than the line source of FIG. 4, eliminating the 1/R fall-off in radial energy dissipation. The programmability and responsiveness of the two dimensional array 12 to form beams in arbitrary directions and from apparent centers in various locations on the surface of the array is used to generate pushed tissue regions of general shape, size, and direction of push by axial and/or lateral sweeping of the focal spot, rapid hopping from one focal spot to from one location to another, or both, taking advantage of the dramatic ratio of propagation speed between longitudinal push waves and shear waves in tissue (order of 100 to 1) to allow formation of an effective source of shear waves which may be of somewhat arbitrary size, shape and orientation such that a focused and steered two- or three-dimensional shear wave beam source of desired orientation, shape and extent may be formed.

In the simple implementation of the present invention shown in FIG. 5, a flat, extended sheet of pushed tissue is excited by push beam sheet 80, which generates shear waves in a flat sheet 90, 93, propagating laterally rather than radially outward, and decreasing the decay with travel distance of the shear wave. This improves the distance of penetration of the various radiation force modalities. This sheet may be formed by focusing deeply within the tissue and starting the transmission of a long burst of ultrasound. While the burst is being transmitted, the focal point is drawn shallower toward the transducer to form a line source. Multiple such lines of push beam force are transmitted within a plane perpendicular to the face of the transducer as shown in FIG. 5. Alternatively the plane of push beam force is transmitted in other planes not perpendicular to the face of the transducer array and within the range of directivity of the array, to generate a planar source of shear waves. Such transmission will effectively produce a unitary push force in two dimensions, so long as the duration of the whole excitation sequence is somewhat faster than the period of the shear waves to be produced. Since longitudinal ultrasound propagation path transit times are of the order of 100 microsec, while the desired shear wave period is of the order of 2 millisec, there is time for numerous transmits to produce the energy sheet 90, 92.

A variation of the transmit technique of FIG. 5 is to transmit a sheet beam which, by simultaneous excitation of elements of the two dimensional transducer array in elevation or azimuth, transmits a sheet beam from the two dimensional array. Since the delay profile of the 2-D array is fully programmable, transmitting a sheet focused deep in the field and then moving the focal point closer at a rate comparable to the shear wave velocity will allow formation of a simple planar shear wave source. This planar source may be transmitted at any rotational angle, so shear waves may be propagated in any lateral direction. Also, the tilt of the planar source may be varied, so the shear wave source may be directed into planes not perpendicular to the array.

A third implementation of the present invention is illustrated in FIG. 6. In this implementation a sheet beam is transmitted by the two dimensional array transducer which is transversely curved, either in space or in delay profile or both, so that the resulting shear wave source focuses into a thin beam, further increasing the resolution and sensitivity of the techniques used to detect it. It is even possible to create a curvature along the axial direction as shown by the push beam sheet (PBS) in FIG. 6, creating two dimensional focusing of the shear waves. As this drawing illustrates, the two dimensional transducer array 12 generates a curved push beam sheet PBS. The curvature of PBS causes the shear wave front SWF to progressively converge as it travels, as indicated by the progressive convergence of SWF1, SWF2, and SWF3 toward the checkered plane 98. This convergence is also indicated by the profile 96 of the curved shear wave fronts. To the right in the drawing is a shear wave front SWF2', illustrating the reverse curvature of the shear wave front as it passes beyond its line of maximum convergence at SWF3. This method of focusing the shear waves is most suitable for a line measuring technique rather than a plane measuring technique. The data collection rate is sharply reduced in exchange for the large increase in sensitivity in the vicinity of the shear wave focus at SWF3. This method can also be used to focus a two dimensional curved shear wavefront to a diffraction-limited point focus or a limited axial depth region.

The diagnoses of tissue stiffness which are performed by measuring shear waves are highly dependent upon precise tracking of the shear wavefront over time, so that its changes in propagation velocity as it passes through different tissues can be accurately measured. In systems of the prior art, these measurements were performed while assuming that there was no relative motion between the ultrasound probe and the tissue, so that the only relative tissue motion is that produced by the push pulse force. This assumption is often incorrect, since relative motion can also be produce by unsteady holding of the probe, patient motion, or anatomical motion due to breathing and heartbeat motion. The displacement caused by radiation force is very small, on the order of 10 µm. Although the precision of ultrasound RF tracking can reach 1-2 µm, the shear wave motion can be buried in much larger patient motion such as cardiac and respiratory motion, as well as environmental interference. While filtering can be used to try to eliminate noise whose frequency is outside the range of the shear wave harmonic frequencies, in accordance with a further aspect of the present invention, an additional step is taken to reduce noise. This consists of using the displacement estimated away from the region of the excitation (for instance, at a depth of at least half of the depth-of-field away from the focus in the depth direction) as the background noise, since it can be assumed that no significant radiation force is applied in that region. This noise "source" in the form of displacement estimates is subtracted from the shear wave displacement estimated at the region of interest.

A simple example of background motion sensing is illustrated in FIG. 7. A single vector push beam, being focused, has its most significant effect along its beam axis near the focal depth 110. FIG. 7 illustrates the profile 100 of a vector push beam in which the force of the push beam is concentrated. Some acoustic radiation force-based elastographic techniques involve only tracking along the same axis as the push beam and in this case, data from the tracking beams already in use can be employed to sense background motion, but from ranges significantly shorter and longer than the focal length, that is, outside the depth of field of the focused push beam, to make an axial motion estimate for subtraction from the sample measurement. The stars 102 and 104 illustrate focal regions of two background tracking beams, one located above the focal region of the push pulse and one located below. The focal regions of the background tracking beams are indicated by the dashed beam profiles on either side of the background tracking beams. Echoes from these background tracking locations are sampled at a plurality of times before, during, and/or after transmission of the push pulse(s). These temporally different echoes are compared, generally by correlation, and the comparison(s) used to assess the presence of axial background motion. Any displacement of the tissue due to background effects is subtracted from motion estimates due to the shear wave to correct estimated shear wave motion for background effects.

FIG. 8 illustrates another example of background motion sensing. In this example, additional locations 106, 107, 108 and 116, 117, 118 located laterally well outside the region of interest 120 of shear wave tracking may be tracked during the measurement interval to acquire data which enables computation of a background motion estimate at any location within or around the region of interest. Motion effects from tilting or rotation of the probe during the measurement interval can be sensed in this way. For instance, if comparisons of echo changes at points 106, 107, 108 over time indicate an upward motion to the left of the region of interest 120, and differences at points 116, 117, 118 indicate a downward motion to the right of the region of interest at the same time, it can be concluded that there is an overall rotational or tilting motion of the probe with respect to the region of interest for which compensation in measurements should be made.

As FIG. 9 illustrates, it is also possible, and in some instances may be desirable, to track in the plane of a 2D image along several lines within the region of interest 120 adjacent to the push region 100, at times before and after the push event. In this example two lines of background motion tracking samples 126, 127, 128 and 136, 137, 138 are sampled periodically during the measurement interval to the left of the push pulse vector 100 and two lines of background motion tracking samples 146, 147, 148 and 156, 157, 158 are sampled to the right of the push pulse vector. Normally, one background motion sampling before and several background motion samplings after a push event are required to obtain a motion estimate due to a push event. However, if two or more background motion sampling ensembles before the push are acquired, an estimate of background motion can also be obtained. If at least one background motion echo ensemble is also acquired a sufficiently long time after the push, additional estimates of background motion may be also be gained, since motion may be interpolated in time from before to a time after the push pulse, rather than extrapolated. This technique may be performed at multiple lateral offsets from the axis of the push beam. If the background motion is not uniform over the region of interest, a scalar field estimate of the axial motion component within the sample volume may be obtained.

It will be appreciated that background motion correction can be performed for measurements made in 3D space in addition to just a plane. The use of a two dimensional array transducer as shown in FIG. 1 enables the performance of elastography in three dimensions to bring improved clinical utility, as out-of-plane variations in elasticity properties can adversely affect the effectiveness of single-plane elastographic measurements. The additional 3D control of push beam geometry by a two dimensional array can enhance signal-to-noise performance and bring additional functionality. In this case, additional background motion tracking beams outside the region of interest during the measurement interval and/or early and late background motion tracking beams may be added within the 3D region of interest as indicated above for the 2D case, to obtain a full 3D volume estimate of axial motion for correction of the measured response to the push beam excitation. For example, four background motion tracking lines can be transmitted at 90° intervals around a push pulse vector. Background motion tracking lines can be transmitted in front of and behind a 2D push pulse sheet as described above to sense tissue motion in a three dimensional space over which shear waves are being measured.

What is claimed is:

1. An ultrasonic diagnostic imaging system for shear wave analysis comprising:
    an ultrasonic array probe having a two dimensional array of transducer elements which are operable to transmit ultrasound waves along a plurality of different vectors in a subject; and
    a beamformer coupled to the two dimensional array to cause the array to transmit a burst of ultrasound waves and move a focal point of the burst during transmission of the burst to form each of a plurality of line sources,
    wherein the beamformer is configured to simultaneously excite the two dimensional array of transducer elements in two dimensions of the array to form a sheet of energy comprised of the plurality of line sources in a push pulse region for generating a shear wave that is one of: (1) a planar shear wave or (2) a semi-planar shear wave, and propagates away from the sheet of energy
    wherein the beamformer is further configured to cause the two dimensional array of transducer elements to transmit tracking pulses along tracking lines within a path of the shear wave and background tracking pulses along background tracking lines outside the path of the shear wave without moving the ultrasonic array probe, wherein the probe is further configured to receive echo signals from points along the tracking lines and background tracking lines,
    wherein the probe is further configured to transmit the tracking pulses and receive the echo signals from points along the tracking lines in a first time interleaved sequence, and
    wherein the probe is further configured to transmit the background tracking pulses and receive the echo signals from points along the background tracking lines in a time interleaved sequence.

2. The ultrasonic diagnostic imaging system of claim 1, wherein the sheet of energy is a planar sheet of energy.

3. The ultrasonic diagnostic imaging system of claim 1, wherein the shear wave is the semi-planar shear wave, and wherein the semi-planar sheet of energy is a curved sheet of energy.

4. The ultrasonic diagnostic imaging system of claim 1, wherein shear wave is the planar shear wave.

5. The ultrasonic diagnostic imaging system of claim 4, wherein the sheet of energy is formed in a plane which is normal to a face of the two dimensional array transducer.

6. The ultrasonic diagnostic imaging system of claim 4, wherein the sheet of energy is formed in a plane which is tilted at a non-orthogonal angle to a face of the two dimensional array transducer.

7. The ultrasonic diagnostic imaging system of claim 1, wherein the two dimensional array is configured to transmit the sheet of energy during a time interval which is less than the time of one cycle of the generated shear wave.

8. The ultrasonic diagnostic imaging system of claim 7, wherein the focal point of the burst is moved both axially and laterally during the time interval.

9. The ultrasonic diagnostic imaging system of claim 1, shear wave is the semi-planar shear wave, and wherein the semi-planar sheet of energy is a curved sheet of energy which produces a shear wave source focused into a line.

10. The ultrasonic diagnostic imaging system of claim 3, wherein the curved sheet of energy produces a shear wave source focused to a diffraction-limited point focus.

11. The ultrasonic diagnostic imaging system of claim 3, wherein the curved sheet of energy produces a shear wave source focused over a limited axial depth region.

12. The ultrasonic diagnostic imaging system of claim 1, further comprising:
    an A-line memory for storing the tracking line echo data; and a display for displaying results of a shear wave measurement.

13. The ultrasonic diagnostic imaging system of claim 1, wherein the probe is configured to form the sheet of energy by sweeping the focal point in an axial direction, a lateral direction, or both.

14. The ultrasonic diagnostic imaging system of claim 1, wherein the probe is configured to form the sheet of energy such that the sheet of energy extends in a depth dimension as well as an elevation dimension.

* * * * *